United States Patent [19]

Chen et al.

[11] 4,442,193

[45] Apr. 10, 1984

[54] PHOTOCONDUCTIVE COMPOSITIONS AND ELEMENTS CONTAINING NAPHTHALENE BIS-DICARBOXIMIDE COMPOUNDS

[75] Inventors: Chin H. Chen; Ralph H. Young; Michael Scozzafava, all of Rochester, N.Y.

[73] Assignee: Eastman Kodak Company, Rochester, N.Y.

[21] Appl. No.: 468,726

[22] Filed: Feb. 22, 1983

[51] Int. Cl.$^3$ .............................................. G03G 5/09
[52] U.S. Cl. ....................................... 430/83; 430/573
[58] Field of Search ..................... 430/83, 76, 90, 95, 430/573

[56] References Cited

U.S. PATENT DOCUMENTS 3,615,411 10/1971 Hessel ................................. 430/83

Primary Examiner—John D. Welsh
Attorney, Agent, or Firm—Torger N. Dahl

[57] ABSTRACT

Photoconductive compositions comprising photoconductors and 1,4,5,8-naphthalene bis-dicarboximide sensitizing compounds are disclosed. Compositions and elements containing such compounds are sensitized to radiation below 400 nm. Embodiments are disclosed in which the photoconductor is an arylalkane leuco base. Such embodiments are advantageously nonsensitive to radiation above 400 nm and are also nonpersistent.

11 Claims, No Drawings

PHOTOCONDUCTIVE COMPOSITIONS AND ELEMENTS CONTAINING NAPHTHALENE BIS-DICARBOXIMIDE COMPOUNDS

FIELD OF THE INVENTION

The present invention relates to photoconductive compositions containing cyclic bis-dicarboximide sensitizers.

Photoconductive compositions are employed in well-known imaging processes involving, for example, charging, imagewise exposure to actinic radiation and development to form a toner image on the composition. To be considered useful, the composition, however, must be adequately sensitive to light so that inordinate degrees of exposure are not required. Efforts to improve the sensitivity of the photoconductive composition have led to a variety of so-called sensitizing compounds which increase the response of the photoconductive composition both in the spectral region where it is intrinsically sensitive and in other spectral regions. While many sensitizing compounds are currently known, continuing research is underway to find new materials.

In addition to the requirement of adequate sensitivity, in certain applications sensitivity below 400 nm only and nonpersistent conductivity are highly desirable. (400 nm represents the approximate spectral wavelength of transition between visible and nonvisible light; persistent conductivity refers to the lingering conductivity of some materials in exposed regions.) Exclusive sensitivity below 400 nm permits development of the photoconductive composition in visible light. It also facilitates use of the photoconductive composition in second-stage operations such as contact printing by transmitting light above 400 nm through the composition onto a second material which is sensitive to the transmitted light.

Nonpersistent conductivity, on the other hand, is important if a photoconductive composition is to be cycled through a charge-expose-develop sequence a number of times in rapid succession. If the photoconductive composition is persistent, unwanted images from preceding sequences will contaminate the image desired.

The requirements of exclusive sensitivity below 400 nm and nonpersistence are difficult to satisfy. Sensitizers meeting these, as well as sensitizing, criteria would be highly desirable.

In accordance with the present invention, we have discovered that certain 1,4,5,8-naphthalene dicarboximide compounds are highly useful as sensitizers with photoconductors in photoconductive compositions. Furthermore, embodiments comprising our sensitizers in combination with arylalkane leuco base photoconductors are advantageously nonpersistent and sensitized to (i.e., absorb) radiation below 400 nm exclusively. The sensitiziers we have discovered to be useful correspond to the structure:

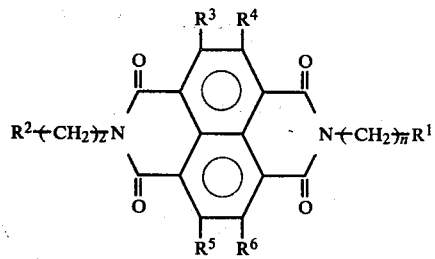

wherein:

$R^1$ and $R^2$, which may be the same or different, represent aryl, such as phenyl or naphthyl, or aryl substituted with alkyl, alkoxy, perfluoroalkyl or perfluoroalkoxy groups having 2 to 20 alkyl carbon atoms; sulfonyl; sulfone; sulfonamide; nitrile; or nitro groups;

$R^3$, $R^4$, $R^5$ and $R^6$, which may be the same or different, represent hydrogen, alkyl having 1 to 4 carbon atoms, alkoxy having 1 to 4 carbon atoms, or halogen; and n is 0 to 3.

Preferably, $R^1$ and $R^2$ in Formula I are phenyl or phenyl substituted with alkyl, alkoxy or perfluoralkyl, and $R^3$, $R^4$, $R^5$ and $R^6$ are hydrogen.

In a preferred embodiment of the invention, the above photoconductive composition is a singlephase homogeneous mixture of the photoconductor, dicarboximide sensitizer and binder, if a binder is desired. To this end, the components of the composition are selected so as to be rendered soluble in common coating solvents such as halogenated hydrocarbon liquids. Preferably, the solubility of the Strcuture I dicarboximide sensitizer in a coating solvent is at least 0.25 percent by weight of the resulting solution, and most preferably at least 1 percent by weight of the solution.

Homogeneous compositions of the present invention are preferably prepared by coating from halogenated hydrocarbon liquids such as 1,2-dichloroethane, 1,1,2-trichloropropane and 1,1,2,2-tetrachloroethane. In this regard, we have found that Structure I dicarboximide sensitizing compounds in which $R_1$ and $R_2$ are substituted phenyl groups having at least one of the above-defined optional substituents provide useful dicarboximide solubility in halogenated hydrocarbon liquids.

Representative 1,4,5,8-naphthalene bis-dicarboximides employed in the defined composition include the compounds listed in Table 1.

TABLE 1

A.

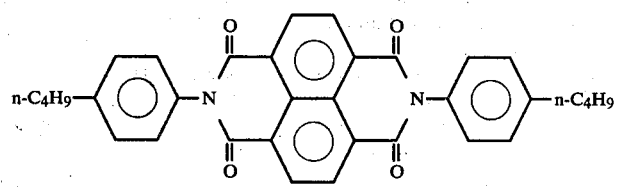

N,N'—bis[p-(n-butyl)phenyl]-1,4,5,8-naphthalene bis-dicarboximide

TABLE 1-continued

B.

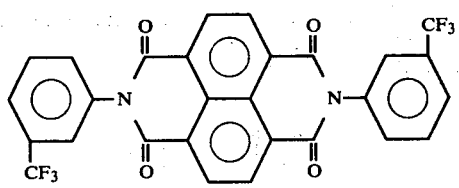

N,N'—bis(m-trifluoromethylphenyl)-1,4,5,8-naphthalene bis-dicarboximide

C.

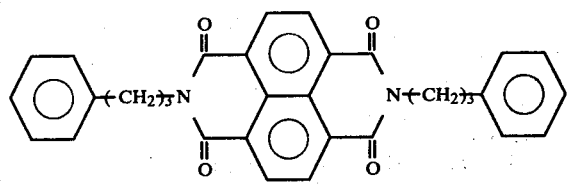

N,N'—bis(3-phenylpropyl)-1,4,5,8-naphthalene bis-dicarboximide

D.

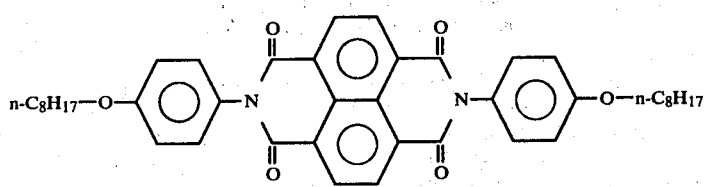

N,N—bis[p-(n-octyloxy)phenyl]-1,4,5,8-naphthalene bis-dicarboximide

E.

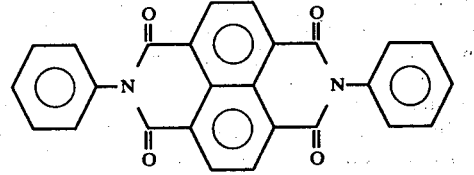

N,N'—bis(phenyl)-1,4,5,8-naphthalene bis-dicarboximide

---

The amount of dicarboximide employed can vary widely in accordance with the degree of sensitization desired. Effective amounts of the sensitizer represented by Structure I can vary widely in order to increase the speed of the photoconductive composition relative to compositions without the sensitizer of Structure I. The optimum concentration in any given case will vary with the specific photoconductor and sensitizing compound used. Substantial speed gains can be obtained where a sensitizer according to Structure I is added in a concentration range from about 0.0001 to about 30 percent based on the weight of the composition on a dry basis. A preferred sensitizer concentration range is from about 0.005 to about 5.0 percent.

The dicarboximide sensitizers used in this invention are effective for enhancing the electrophotosensitivity of a wide variety of photoconductors. Representative photoconductors useful in compositions containing the present sensitizers are described below:

(1) arylamine photoconductors including substituted and unsubstituted arylamines, diarylamines, nonpolymeric triarylamines and polymeric triarylamines such as those described in U.S. Pat. No. 3,240,597 by Fox issued Mar. 15, 1966, and U.S. Pat. No. 3,180,730 by Klupfel et al issued Apr. 27, 1965;

(2) polyarylalkane photoconductors of the types described in U.S. Pat. No. 3,274,000 by Noe et al issued Sept. 20, 1966, U.S. Pat. No. 3,542,547 by Wilson and U.S. Pat. No. 3,542,544 by Seus et al, both issued Nov. 24, 1970;

(3) 4-diarylamino-substituted chalcones of the types described in U.S. Pat. No. 3,526,501 by Fox issued Sept. 1, 1970;

(4) nonionic cycloheptenyl compounds of the types described in U.S. Pat. No. 3,533,786 by Looker issued Oct. 13, 1970;

(5) compounds containing an:

$$>N-N<$$

nucleus, as described in U.S. Pat. No. 3,542,546 by Fox issued Nov. 24, 1970;

(6) organic compounds having a 3,3'-bis-aryl-2-pyrazoline nucleus, as described in U.S. Pat. No. 3,527,602 by Fox et al issued Sept. 8, 1970;

(7) triarylamines in which at least one of the aryl radicals is substituted by either a vinyl radical or a vinylene radical having at least one active hydrogen-containing group, as described in U.S. Pat. No. 3,567,450 by Brantly et al issued Mar. 2, 1971;

(8) triarylamines in which at least one of the aryl radicals is substituted by an active hydrogen-containing group, as described in Belgian Pat. No. 728,563 by Brantly et al dated Apr. 30, 1969;

(9) any other organic compound which exhibits photoconductive properties such as those set forth in U.S. Pat. No. 3,250,615 and Australian Pat. No. 248,402 and the various polymeric photoconductors such as the photoconductive carbazole polymers described in U.S. Pat. No. 3,421,891 issued Jan. 14, 1969.

In preferred photoconductive compositions, arylalkane leuco base photoconductors are the principal photoconductive constituents. Such preferred compositions are advantageously nonpersistently conductive and sensitive to radiation below 400 nm, but substantially insensitive to radiation above 400 nm. Arylalkane leuco base photoconductors are disclosed, for example, in U.S. Pat. No. 3,542,547 above and bear the structure:

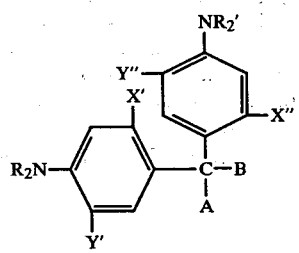

wherein:

each of R and R' is selected from the group consisting of hydrogen, alkyl and aralkyl having 1 to 4 carbon atoms in the alkyl group;

each of X' and X" is selected from the group consisting of alkyl having 1 to 4 carbon atoms, alkoxy having 1 to 4 carbon atoms, hydroxyl and halogen;

each of Y' and Y" is selected from the group consisting of alkyl having 1 to 4 carbon atoms, alkoxy having 1 to 4 carbon atoms, hydroxyl, halogen and hydrogen; and each of A and B is:
(1) hydrogen, with the proviso that A and B are not both hydrogen;
(2) aryl such as phenyl, α-naphthyl, β-naphthyl, 9-anthryl and substituted derivatives thereof wherein the substituent is dialkylamino, alkylamino, amino, alkyl, alkoxy, hydroxyl or halogen;
(3) an aliphatic alkyl group having 1–18 carbon atoms, e.g., methyl, ethyl, propyl, butyl, isobutyl, octyl, dodecyl, etc., including a substituted alkyl group having 1–18 carbon atoms;
(4) a cycloalkyl group having 4–8 carbon atoms in the cyclic nucleus, e.g., cyclobutyl, cyclohexyl, cyclopentyl, etc., including a substituted cycloalkyl group; or
(5) a cycloalkenyl group having 4–8 carbon atoms in the cyclic nucleus, e.g., cyclohex-3-enyl, cyclopent-3-enyl, cyclobut-2-enyl, cyclohex-2-enyl, etc., including a substituted cycloalkenyl group.

Representative Formula II arylmethane photoconductors are set forth in Table 2 below.

TABLE 2

(1) 4,4'-bis(diethylamino)-2,2'-dimethyltriphenylmethane
(2) 4,4'-bis(diethylamino)-2,5-dichloro-2',2"-dimethyltriphenylmethane
(3) 4,4'-bis(diethylamino)-2,2'-dimethyldiphenyl-α-naphthylmethane
(4) 2',2"-dimethyl-4,4',4"-tris(dimethylamino)triphenylmethane
(5) 4',4"-bis(diethylamino)-4-dimethylamino-2',2",5,5"-tetramethyltriphenylmethane
(6) 4',4"-bis(diethylamino)-2-chloro-2',2"-dimethyl-4-dimethylaminotriphenylmethane
(7) 4',4"-bis(diethylamino)-4-dimethylamino-2,2',2"-trimethyltriphenylmethane
(8) 4',4"-bis(dimethylamino)-2-chloro-2',2"-dimethyltriphenylmethane
(9) 4',4"-bis(dimethylamino)-2',2"-dimethyl-4-methoxytriphenylmethane
(10) 4,4'-bis(benzylethylamino)-2,2"-dimethyltriphenylmethane
(11) 4,4'-bis(diethylamino)-2,2',5,5"-tetramethyltriphenylmethane
(12) 4,4'-bis(diethylamino)-2,2'-diethoxytriphenylmethane
(13) 4,4'-bis(diethylamino)-2,2'-dimethyldiphenyl-β-naphthylmethane
(14) 4,4'-bis(diethylamino)-2,2'-dimethyldiphenyl-9-anthrylmethane
(15) 4,4',4"-trisdiethylamino-2,2',2"-trimethyltriphenylmethane
(16) 1,1-bis(4-N,N—diethylamino-2-chlorophenyl)-2-phenylethane
(17) 1,1-bis(4-N,N—diethylamino-2-methoxyphenyl)-2-phenylethane
(18) bis(4-N,N—diethylaminophenyl)cyclopent-2-enylmethane
(19) bis(4-N,N—diethylamino-2-methylphenyl)cyclobut-2-enylmethane
(20) 1,1-bis(4-N,N—diethylaminophenyl)-3-phenylpropane
(21) 1,1-bis(4-N,N—diethylaminophenyl)-2-phenylethane
(22) 1,1-bis(N,N—diethylaminophenyl)butane
(23) bis(4-N,N—diethylaminophenyl)cyclohexylmethane
(24) 1,1-bis(4-N,N—diethylaminophenyl)-2-methylpropane
(25) 1,1-bis(4-N,N—diethylaminophenyl)heptane
(26) bis(4-N.N—d,iethylaminophenyl)cyclohex-3-enylmethane
(27) 1,1-bis(4-N,N—diethylaminophenyl)-2-ethylhexane
(28) 1,1-bis(4-N,N—diethylamino-2-methylphenyl)-3-phenylpropane
(29) 1,1-bis(4-N,Ndiethylamino-2-methylphenyl)-2-phenylethane
(30) 1,1 bis(4-N,N—diethylamino-2-methylphenyl)butane
(31) 1,1-bis(4-N,N—diethylamino-2-methylphenyl)cyclohexylmethane
(32) 1,1-bis(4-N,N—diethylamino-2-methylphenyl)-2-methylpropane
(33) 1,1-bis(4-N,N—diethylamino-2-methylphenyl)butane
(34) bis(4-N,N—diethylamino-2-methylphenyl)cyclohex-3-enylmethane
(35) bis(4-N,N—diethylamino-2-methylphenyl)-4-methylphenylmethane
(36) bis(4-diethylamino)-1,1,1-triphenylethane
(37) bis(4-diethylamino)tetraphenylmethane
(38) 1,1-bis(4-N,N—diethylaminophenyl)cyclohexane
(39) 1,1-bis(4-di-p-tolylaminophenyl)cyclohexane
(40) 1,1-bis(4-di-p-tolylaminophenyl)-2-methylpropane
(41) 1,1-bis(4-N,N—diethylaminophenyl)-4-methylcyclohexane
(42) 1,1-bis(4-N,N—dipropylaminophenyl)cyclohexane
(43) 1,1-bis(4-N,N—diethylaminophenyl)-1-(4-methylphenyl)ethane
(44) 4,4'-bis(diethylamino)-4",4'"-dichlorotetraphenylmethane
(45) 4,4'-bis(dipropylamino)tetraphenylmethane
(46) 4,4'-bis(diethylamino)-4"-isopropyl-2,2'-dimethyltriphenylmethane Particularly useful compositions of the present invention comprise crystallization-inhibiting mixtures of two or more of the arylalkane leuco base photoconductors as disclosed in U.S. Pat. No. 4,301,226 issued Nov. 17, 1981, to L. E. Contois et al. A preferred crystallization-inhibiting mixture comprises three arylmethane photoconductors: bis(4-N,N-diethylamino-2-methylphenyl)-4-methylphenylmethane, 1,1-bis(4-N,N-diethylamino-2-methylphenyl)-2-methylpropane and 4,4'-bis(diethylamino)-2,2'-dimethyltriphenylmethane.

The total amount of photoconductor in the defined composition may vary widely, but preferably ranges from about 5 to about 40 weight percent based on the solvent-free weight of the layer.

Compositions of the present invention are incorporated into an electrically insulating binder and coated as photoconductive layers on an electrically conductive support to form a photoconductive element. The elements so formed are employed in electrophotographic processes to form toned images in a conventional manner.

Preferred electrically insulating binders for use in preparing the photoconductive layers are film-forming, hydrophobic polymeric binders having fairly high dielectric strength. Materials of this type comprise styrene-butadiene copolymers; silicone resins; styrene-alkyd resins; silicone-alkyd resins; soya-alkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetals) such as poly(vinyl butyral); polyacrylic and polymethacrylic esters such as poly(methyl methacrylate), poly(n-butyl methacrylate), poly(isobutyl methacrylate); polystyrene; nitrated polystyrene; polymethylstyrene; isobutylene polymers; polyesters such as poly[ethylene-co-alkylenebis(alkyleneoxyaryl)-phenylenedicarboxylate]; phenolformaldehyde resins; ketone resins; polyamides; polycarbonates; polythiocarbonates; poly[ethylene-co-isopropylidene-2,2-bis(ethyleneoxyphenylene)terephthalate]; copolymers of vinyl haloarylates; poly(ethylene-co-neopentyl terephthalate); and vinyl acetate such as poly(vinyl-m-bromobenzoate-co-vinyl acetate).

Suitable supporting materials for the photoconductive layers of the present invention can include any electrically conducting support. Examples include conducting papers, aluminum-paper laminate, metal foils such as aluminum and zinc foils; metal plates such as aluminum, copper, zinc, brass and galvanized plates, vapor-deposited metal layer (silver, nickel, aluminum) on conventional film supports such as cellulose acetate, poly(ethylene terephthalate), polystyrene and the like.

A useful conducting support can be prepared by coating a transparent film support such as poly(ethylene terephthalate) with a layer containing a semiconductor dispersed in a resin. A suitable conducting coating can be prepared from the sodium salt of a carboxyester lactone of a maleic anhydride-vinyl acetate copolymer or cuprous iodide or the like.

Useful techniques for forming electrophotographic elements and using such elements are described in greater detail in U.S. Pat. Nos. 4,301,226, 3,245,833, 3,267,807 and 3,007,901.

The following examples are provided to aid in the understanding of the present invention.

Preparation of
N,N'-bis[p-(n-butyl)phenyl]-1,4,5,8-naphthalenebis(dicarboximide) (Table 1, Compound A)

A mixture of 30 g (0.11 M) of 1,4,5,8-naphthalenetetracarboxylic dianhydride and 33.4 g (0.22 M) of p-(n-butyl)aniline in 500 mL of phenyletherbiphenyl-eutectic (bp 258° C.) was azeotropically refluxed for 15 hr. After cooling to room temperature, the crystallized solid was filtered and washed with ether until the filtrate turned colorless, to give approximately 50 g of crude Compound A. This was dissolved in 800 mL of hot chloroform; some activated charcoal was added and the mixture cooled to room temperature. The mixture was filtered over diatomaceous earth and the clear, light brown filtrate was concentrated on a steam bath to approximately 400 mL from which 40 g of product was obtained. Further purification was achieved by recrystallization from 2 L of p-dioxane to give 31 g (53%) of pure Compound A as a slightly yellowish solid, mp 358°–360° C.

Preparation of
N,N'-bis(m-trifluoromethylphenyl)-1,4,5,8-naphthalenebis(dicarboximide) (Table 1, Compound B)

A mixture of 4.1 g (0.015 M) of 1,4,5,8-naphthalenetetracarboxylic dianhydride and 4.9g (0.03 M) of m-(trifluoromethyl)aniline in 150 mL of phenyletherbiphenyl-eutectic mixture was azeotropically refluxed overnight. The precipitated solid, on cooling, was filtered, washed with ether and dissolved in 500 mL of methylene chloride. The insoluble black impurities were removed by filtration over diatomaceous earth and the clear filtrate reduced in volume in a rotary evaporator. The residue was recrystallized from 250 mL of acetonitrile to give 2.5 g of pure Compound B: mp 349°–350° C.

Preparation of
N,N'-bis[p-(n-octyloxy)phenyl]-1,4,5,8-naphthalenebis(dicarboximide) (Table 1, Compound D)

A mixture of 3.1 g (0.0114 M) of 1,4,5,8-naphthalenetetracarboxylic dianhydride and 5.07 g (0.0229 M) of p-(n-octyloxy)aniline in 150 mL of phenyletherbiphenyl-eutectic mixture was azeotropically refluxed overnight. The precipitated solid obtained on cooling was filtered, washed thoroughly with ether and boiled in 300 mL of 1% KOH with stirring for 1 hr. The insoluble solid was filtered, washed with water, air-dried and recrystallized from 400 mL of toluene to give 4.25 g (55%) of pure Compound D: mp 346°–348° C.

The following examples illustrate the use of dicarboximide compounds from Table 1 in a photoconductive element of the present invention.

EXAMPLE 1

A solution was prepared with 2 g of Lexan 145 ™ binder (a poly[4,4'-isopropylidenediphenylene carbonate] available from General Electric Company), 0.8 g of Compound I of Table 2 and 0.029 g of Compound A, Table 1, in 20 mL of methylene chloride. The solution was heated gently for about 1 hr and was then coated at 26° C. to a wet thickness of 100 μm on the barrier layer of a conductive film support. The support included a cellulose nitrate barrier layer overlying a cuprous iodide conducting layer on a polyethylene terephthalate substrate. The film was placed in a drying oven overnight at 65° C. to produce a dry, homogeneous photoconductive layer. The dry thickness of the film was 8 μm.

The coated photoconductive layer had absorption peaks at 360 nm (optical density, O.D., of 0.51) and 380 nm (O.D. of 0.43). There was a sharp cutoff in the absorption at 400 nm. (At 400 nm, the O.D. was 0.1, and at 416 nm, the O.D. was 0.02). The element was clear and appeared colorless to the naked eye. The element exhibited substantially no persistent conductivity.

Photodischarge measurements

At $\lambda=380$ nm, $+1000$ V→$+500$ V, 120 ergs/cm$^2$.
At $\lambda=380$ nm, $+600$ V→$+300$ V, 144 ergs/cm$^2$.
At $\lambda=380$ nm, $+600$ V→$+400$ V, 72 ergs/cm$^2$.

At 380 nm, the film absorbed 63% of the incident light.

EXAMPLE 2

The procedure of Example 1 was repeated substituting Compound D for Compound A, Table 1. This film also possessed absorption peaks at 360 nm (O.D.=0.51) and 380 nm (O.D.=0.42). The layer absorbed 62% of the light at 380 nm. The coating was clear and nearly colorless. Photodischarge speed: at 380 nm, $+1100$ V→$+550$ V, 119 ergs/cm$^2$. The element was nonpersistent.

EXAMPLE 3

The procedure of Example 1 was repeated substituting Compound B for Compound A, Table 1. Absorption peaks were observed at 360 nm (O.D.=0.34) and 380 nm (O.D.=0.37). A sharp cutoff in the absorption was observed at 400 nm (O.D.=0.01). The film was clear and appeared colorless to the naked eye.

Photodischarge speed

At 380 nm, $+1000$ V→$+500$ V, 82.7 ergs/cm$^2$.
At 380 nm, $+600$ V→$+300$ V, 132 ergs/cm$^2$.

At 380 nm, the dye absorbed 58% of the incident lihgt. The element was nonpersistent.

Although the invention has been described in considerable detail with particular reference to certain preferred embodiments thereof, variations and modifications can be effected within the spirit and scope of the invention.

We claim:

1. A photoconductive composition comprising a photoconductor and a 1,4,5,8-naphthalene bis-dicarboximide sensitizing compound having the structure:

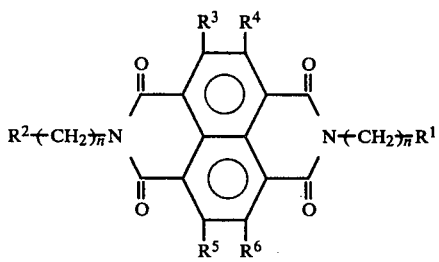

wherein:
R$^1$ and R$^2$, which may be the same or different, represent aryl, or aryl substituted with alkyl, alkoxy, perfluoroalkyl or perfluoroalkoxy groups having 2 to 20 alkyl carbon atoms; sulfonyl; sulfone; sulfonamide; nitrile; or nitro groups;
R$^3$, R$^4$, R$^5$ and R$^6$, which may be the same or different, represent hydrogen, alkyl having 1 to 4 carbon atoms, alkoxy having 1 to 4 carbon atoms or halogen; and
n is 0 to 3.

2. A composition as in claim 1 wherein said dicarboximide compound is selected from the group consisting of N,N-bis[p-(n-butyl)phenyl]-1,4,5,8-naphthalene bis-dicarboximide, N,N-bis(m-trifluoromethylphenyl)-1,4,5,8-naphthalene bis-dicarboximide, N,N-bis(3-phenylpropyl)-1,4,5,8-naphthalene bis-dicarboximide, N,N-bis[p-(n-octyloxy)phenyl]-1,4,5,8-naphthalene bis-dicarboximide and N,N-bis(phenyl)-1,4,5,8-naphthalene bis-dicarboximide.

3. A composition as in claim 1 wherein said photoconductor has the structure:

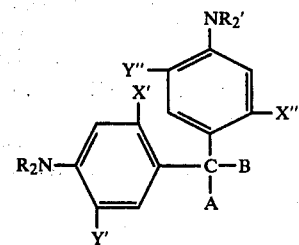

wherein:
each of R and R' is selected from the group consisting of hydrogen, alkyl and aralkyl having 1 to 4 carbon atoms in the alkyl group;
each of X' and X" is selected from the group consisting of alkyl having 1 to 4 carbon atoms, alkoxy having 1 to 4 carbon atoms, hydroxyl and halogen;
each of Y' and Y" is selected from the group consisting of alkyl having 1 to 4 carbon atoms, alkoxy having 1 to 4 carbon atoms, hydroxyl, halogen and hydrogen; and
each of A and B is:
(1) hydrogen, with the proviso that A and B are not both hydrogen;
(2) aryl;
(3) an aliphatic alkyl group having 1–18 carbon atoms;
(4) a cycloalkyl group having 4–8 carbon atoms in the cyclic nucleus; or
(5) a cycloalkenyl group having 4–8 carbon atoms in the cyclic nucleus.

4. A homogeneous photoconductive composition comprising a polymeric binder, an arylalkane leuco base, a photoconductor and a 1,4,5,8-naphthalene bis-dicarboximide sensitizing compound having the structure:

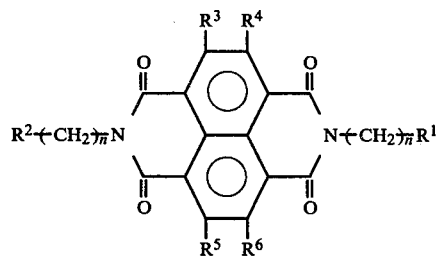

wherein:
R$^1$ and R$^2$, which may be the same or different, represent aryl, or aryl substituted with alkyl, alkoxy, perfluoroalkyl or perfluoroalkoxy groups having 2 to 20 alkyl carbon atoms; sulfonyl; sulfone; sulfonamide; nitrile; or nitro groups;
R$^3$, R$^4$, R$^5$ and R$^6$, which may be the same or different, represent hydrogen, alkyl having 1 to 4 carbon atoms, alkoxy having 1 to 4 carbon atoms, or halogen;

and n is 0 to 3.

5. A homogeneous composition as in claim 4 wherein said dicarboximide sensitizer is soluble in a halogenated hydrocarbon liquid to at least 0.25 percent by weight of total solution.

6. A homogeneous composition as in claim 4 wherein said dicarboximide compound is selected from the group consisting of N,N-bis[p-(n-butyl)phenyl]-1,4,5,8-naphthalene bis-dicarboximide, N,N-bis(m-trifluoromethylphenyl)-1,4,5,8-naphthalene bis-dicarboximide, N,N-bis(3-phenylpropyl)-1,4,5,8-naphthalene bis-dicarboximide and N,N-bis[p-(n-octyloxy)phenyl]-1,4,5,8-naphthalene bis-dicarboximide.

7. A homogeneous composition as in claim 4 wherein the concentration of said dicarboximide compound is at least 1 percent by weight of said composition on a solvent-free basis.

8. A homogeneous composition as in claim 4 wherein said arylalkane leuco base photoconductor has the structure:

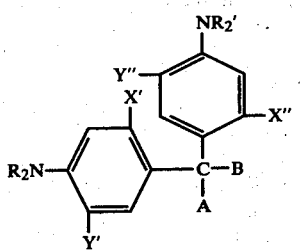

wherein:

each of R and R' is selected from the group consisting of hydrogen, alkyl and aralkyl having 1 to 4 carbon atoms in the alkyl group;

each of X' and X" is selected from the group consisting of alkyl having 1 to 4 carbon atoms, alkoxy having 1 to 4 carbon atoms, hydroxyl and halogen;

each of Y' and Y" is selected from the group consisting of alkyl having 1 to 4 carbon atoms, alkoxy having 1 to 4 carbon atoms, hydroxyl, halogen and hydrogen; and each of A and B is:
(1) hydrogen, with the proviso that A and B are not both hydrogen;
(2) aryl;
(3) an aliphatic alkyl group having 1–18 carbon atoms;
(4) a cycloalkyl group having 4–8 carbon atoms in the cyclic nucleus; or
(5) a cycloalkenyl group having 4–8 carbon atoms in the cyclic nucleus.

9. A homogeneous composition as in claim 8 comprising the three leuco base photoconductors bis(4-N,N-diethylamino-2-methylphenyl)-4-methylphenylmethane, 1,1-bis(4-N,N-diethylamino-2-methylphenyl)-2-methylpropane and 4,4'-bis(diethylamino)-2,2'-dimethyltriphenylmethane.

10. A photoconductive element comprising an electrically conducting support and a layer of the photoconductive composition of claim 1.

11. A photoconductive element comprising an electrically conducting film support and a layer of the homogeneous photoconductive composition of claims 4, 6, 8 or 9.

* * * * *